United States Patent [19]

Hill

[11] Patent Number: 4,864,041

[45] Date of Patent: Sep. 5, 1989

[54] TRANSITION METAL-SUBSTITUTED POLYOXOMETALATES AS CATALYSTS FOR HOMOGENOUS LIQUID-PHASE ORGANIC OXIDATION PROCESSES

[75] Inventor: Craig L. Hill, Atlanta, Ga.

[73] Assignee: Emory University, Atlanta, Ga.

[21] Appl. No.: 10,682

[22] Filed: Feb. 4, 1987

[51] Int. Cl.$^4$ ............................................. C07C 30/03
[52] U.S. Cl. .................... 549/513; 549/524; 549/529; 549/531; 549/533; 549/546; 556/14
[58] Field of Search ............... 549/533, 531, 529, 546, 549/513, 524; 556/14

[56] References Cited

U.S. PATENT DOCUMENTS

| | | | |
|---|---|---|---|
| 2,870,171 | 1/1959 | Gable | 549/531 |
| 3,156,709 | 11/1964 | Allan | 549/531 |
| 3,293,269 | 12/1966 | Wolgemuth | 549/531 |
| 3,666,777 | 5/1972 | Sorgenti | 549/529 |
| 3,935,272 | 1/1976 | Chapurlat | 549/524 |
| 3,993,672 | 11/1976 | Arzoumanian et al. | 549/533 |
| 4,511,745 | 4/1985 | Bergman et al. | 570/241 |
| 4,612,301 | 9/1986 | Currie et al. | 502/154 |

OTHER PUBLICATIONS

*J. Inorg. Nucl. Chem.*, 1967, vol. 29, pp. 2935–2944; Pergamon Press Ltd., Printed in Northern Ireland.
*C.R. Acad. Sc. Paris*, t.266 (4 Mar. 1986), pp. 702–704, Series C.
*C.R. Acad. Sc. Paris*, t.266 (29 Apr. 1968), pp.1363–1365.
CA 102:87457 which discloses the Photocatalytic Generation of Hydrogen . . .
CA 96.216987g which discloses the Use of Molybdotungstophosphoric Acid . . .
*J.A.C.S.* (1986), vol. 108, pp. 536–538 which discloses the Oxidation of . . .
CA 99.52841p which discloses the Catalytic Oxidation of Alkanes by . . .
*J.A.C.S.* (1986), vol. 108, pp. 3528–3529 which discloses the Homogenous . . .
CA 102:7251r which discloses V— and P— containing Crystalline Oxides . . .
CA 99:63147t which discloses the Synthesis and Some Physical Chemical . . .
CA 103:70606w which discloses the use of Certain Heteropolyacids as . . .
*J. Chem. Soc., Chem. Commun.* (1982), pp. 12–13 which discloses the . . .
*Inorganica. Chimica. Aceta.*, 46 (1980) 155–158 which discusses the . . .
*J. Chem. Soc. Dalton Trans.* (1986), 1669–1675 which discloses the . . .
*Inorg. Chem.* (1986), 25, 4386–4389 which discloses the Vanadium . . .
*Inorg. Chem.*, (1985), 24, 439–441 which discloses the Photocatalytic . . .
*J. Chem. Soc., Chem. Commun.*, (1982), pp. 12–13 which discloses the . . .
*J.A.C.S.* (1984) vol. 106, pp. 2737–2738 which discloses the Chemistry of . . .
*J. Chem. Soc. Dalton Trans* (1984), pp. 793–799 which discloses the . . .
*Inorganica Chemica Aceta* 87 (1984) 177–180 which discloses the . . .
*J. Chem. Soc. Dalton Trans.* (1985) pp. 395–199 which discloses the use of . . .
*J. Phy. Chem. (1984), 88, 4210–4213 which discloses Photocatalytic* . . .
Yamase, "Photochemistry of Polyoxometalates as Homogenous". . .
Geletii, et al., "Catalytic Oxidation of Alkanes by Molecular Oxidation". . .
Science, Jun. 16, 1986, pp. 15–16 which discloses the Use of Soluble . . .
*J. Chem. Soc., Chem. Commun*, 1984, pp. 279–280.

*Primary Examiner*—Richard L. Raymond
*Assistant Examiner*—Raymond Covington
*Attorney, Agent, or Firm*—Oblon, Spivak, McClelland, Maier & Neustadt

[57] ABSTRACT

A novel process for the homogenous oxidation of organic substrates is disclosed. This process uses a transition metal-substituted polyoxometalate catalyst, which in the presence of an oxygen donor, catalyses the carbon-hydrogen bond (e.g., alkane) hydroxylation reaction and/or epoxidation reaction of the organic substrate.

20 Claims, 1 Drawing Sheet

TRANSITION METAL-SUBSTITUTED POLYOXOMETALATES AS CATALYSTS FOR HOMOGENOUS LIQUID-PHASE ORGANIC OXIDATION PROCESSES

BACKGROUND OF THE INVENTION

1. Field of the Invention

This invention relates to homogeneous liquid-phase catalytic oxidation processes and to catalysts used in these processes.

2. Discussion of the Background

Catalysts are substances which facilitate reactions. At a given temperature, a catalyst accelerates the rate of a reaction. The term "catalyst" in this document is used in accordance with this standard meaning.

Catalysis is broken down into two different and unrelated classes of catalysis: (1) heterogeneous catalysis; and (2) homogeneous catalysis. In heterogeneous catalysis, the reaction mixture contains materials in at least two different physical states. Generally, the catalyst is in the form of a solid, and the substrate and product are in the form of either liquids and/or gases. Heterogeneous catalysis is characterized by high temperatures, high pressures and lower selectivity. This is the form of catalysis typically used in large-scale industrial applications (e.g., oil refining and coal liquefaction).

In homogeneous catalysis the reaction mixture is essentially made up of one physical phase. The catalyst, the substrate and the product are all typically dissolved in the reaction mixture. Homogeneous catalysis is characterized by lower temperatures, lower pressures and higher selectivity as compared to heterogeneous catalysis. It thus requires less energy and can be used on more sensitive substrates which could not withstand the temperature and pressure regiment of heterogeneous catalysis.

Because of the very nature of heterogeneous catalysis and homogeneous catalysis, catalysts used in heterogeneous catalysis and catalysts used in homogeneous catalysis are considered to be two distinct and different systems in the art of catalysis. A heterogeneous catalyst is essentially always an insoluble solid material designed to withstand the adverse environment of heterogeneous catalysis without loss of its catalytic activity. A heterogeneous catalyst is designed to remain insoluble in the reaction medium to facilitate separation of the catalyst from the rest of the reaction mixture upon completion of the reaction.

Heterogeneous catalysts are typically inorganic materials selected on the basis of their ability to remain insoluble in the reaction medium, and withstand high temperatures and high pressures without change. Examples of typical heterogeneous catalysts include zeolites and transition metals supported on an inorganic matrix.

By contrast, homogeneous catalysts are materials which are selected because of their ability to dissolve in the reaction medium where they exhibit catalytic activity. Homogeneous catalysts are typically materials which, at a molecular level, possess a large organic component. Transition metals coordinated to various organic ligands are typical homogeneous catalysts. Homogeneous catalysts are thus selected on the basis of their ability to dissolve in the reaction medium and to exhibit selective catalytic activity.

Since only a limited number of elements are available, one will, of course, be able to find structurally similar materials used both in heterogeneous and homogeneous catalysts. But this overlap is only accidental, and, in the art of catalysis, a material's catalytic activity in a heterogeneous catalytic environment does not suggest its use in a homogeneous catalytic system, and vice a versa.

The partial oxidation of organic substrates using either homogeneous or heterogeneous catalysts is one of the most important processes used to transform organic substrates into desired materials or intermediates used in the production of desired materials. For example, the partial oxidation reaction of hydrocarbons is one of the most applied processes for converting hydrocarbons into valuable chemical intermediates.

Typical examples of homogeneous catalyst catalyzed oxidation reactions include the partial oxidation of hydrocarbons: (1) the oxidation of carbon-hydrogen bonds (e.g., alkanes)) to the corresponding alcohol, also known as the carbon-hydrogen bond (e.g., alkane) hydroxylation reaction; and (2) the epoxidation of alkenes.

A not so considerable but substantial and growing amount of work has been done on the catalytic homogeneous oxidation of alkanes to obtain the corresponding alcohol (this process is also known as alkane hydroxylation or carbon-hydrogen bond hydroxylation), illustrated in equation (1) below:

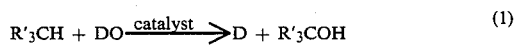

(DO = oxygen donor; R' = $C_{1-30}$ alkyl or hydrogen)

Considerable work has been done on the catalytic homogeneous epoxidation of alkenes, illustrated in equation (2) below:

(DO = oxygen donor)

The most established technology in the homogeneous epoxidation of alkenes is the epoxidation of olefins by alkyl hydroperoxides catalyzed by mononuclear early transition metal complexes. These epoxidation reactions use typically titanium, vanadium, and molybdenum species. See for example, *Aldrichimica Acta*, Vol. 12, No. 4, pp. 63-73 (1979) summarizes much of this type of oxidation reaction. *J. Org. Chem.*, 1986, 51, 1922-1925 and *Chemical and Engineering News*, page 24, June 2, 1986 specifically focus on the application of epoxidation reactions to chiral epoxidation. These early-transition-/alkylhydroperoxide epoxidation processes have not been observed to be active for the activation and functionalization of alkanes.

Metalloporphyrins and high valent oxometalloporphyrin intermediates include biological materials which function as homogeneous catalysts capable of attacking both alkenes and alkanes. One of these biological materials, cytochrome P-450, is the most potent oxidant of organic molecules in the biosphere. This enzyme can utilize dioxygen plus electrons to oxidize substrates, or like the metalloporphyrins and other synthetic active site analogs, cytochrome P-450 can utilize oxygen donors to oxidize substrates.

The principal academic work on the homogeneous catalytic alkane functionalization systems appeared in several papers, principally in 1983. Two principal papers are: J. A. Smegal and C. L. Hill, *J. Am. Chem. Soc.*, 1983, 105, 3515 and J. T. Groves and T. E. Nemo, *J.*

*Am. Chem. Soc.*, 1983, 105, 6243. The Groves paper addresses the Fe$^{III}$TPP(X)/iodosylbenzene system (TPP=the tetraphenylporphyrinato dianion ligand). The Smegal paper gives a fairly complete discussion of the mechanism of catalytic alkane functionalization by the MnTPP(X)/iodosylbenzene system.

All of the homogeneous catalytic oxygen atom transfer oxidation systems discussed above rely on the use of catalysts that contain organic ligands. Inasmuch as all organic ligands are inherently unstable with respect to oxidation by dioxygen as well as to oxidation by strong oxidizing agents which include oxygen donors, the oxidative instability of these catalysts has been the limiting factor to their success in these processes.

In the epoxidation processes, and particularly in alkane hydroxylation processes, oxidative degradation renders homogeneous catalysts inactive after as little as 50 turnovers. (A turnover is one interaction between the catalyst and a substrate molecule to produce a product molecule.)

Prior to the present invention the most stable catalytic system for homogeneous catalytic oxygen atom transfer oxidation of hydrocarbons via oxometal intermediates was the system constituted by the oxidatively resistant metalloporphyrin, tetrakis(2,6-dichlorophenyl)porphinato-iron(III) chloride (FeTDCPPCl) and the highly reactive oxidatively resistant oxygen donor, pentafluoroiodosylbenzene (PFIB). These systems which are disclosed and discussed in Traylor et al., *J. Chem. Soc., Chem. Commun.*, 1984, 279 are however still not stable enough to permit their use in an economic setting.

Thus, in view of the numerous advantages inherent to homogeneous catalysis which is unfortunately limited by the stability of the catalytic materials used therein, there exists a strongly felt need for a new process for the homogeneous catalytic oxidation of organic substrates. Such a new process should ideally be based on a catalyst which would provide the advantages of homogeneous catalysis, e.g., selective oxidation of organic substrates at low temperatures and low pressure requirements, without suffering from the drawbacks which have heretofore limited homogeneous catalysis, especially including catalyst sensitivity to the reaction medium and conditions.

SUMMARY OF THE INVENTION

Accordingly, it is an object of this invention to provide a novel process for the homogeneous oxidation of varied organic substrates.

It is another object of this invention to provide a novel process for the homogeneous carbon-hydrogen bond hydroxylation of organic substrates.

It is another object of this invention to provide the novel process for the epoxidation of organic substrates.

It is another object of this invention to provide a novel process for the homogeneous oxidation of organic substrates, where the process uses a catalyst which does not suffer from degradation traditionally observed with homogeneous oxidation catalysts.

It is another object of this invention to provide novel homogeneous oxidation catalysts which can be used to advantage in homogeneous oxidation processes because they do not suffer from degradation as is observed with traditional homogeneous oxidation catalysts.

The inventor has now discovered a process which satisfies all of the objects of this invention outlined above, and other objects which will become obvious from the description of the invention given hereinbelow. The present invention thus relates (1) to a process for the catalytic oxidation of an organic substrate, and (2) to novel homogeneous oxidation catalysts.

The process comprises contacting at least one organic substrate containing a carbon-hydrogen bond or an olefinic group with a transition metal-substituted polyoxometalate and an oxygen donor to obtain a homogeneous catalytic reaction medium from which a product corresponding to an oxidized form of the substrate is obtained. The transition metal-substituted polyoxometalates used in the present invention are characterized by the fact that (1) the transition metal (defined infra) is encased or ligated by several oxygen atoms of the metal oxide framework of the polyoxometalate, and (2) that this transition metal has at least one coordination site available for coordination with either the oxygen donor or the substrate or both.

DETAILED DESCRIPTION OF THE PREFERRED EMBODIMENTS

Figure 1:
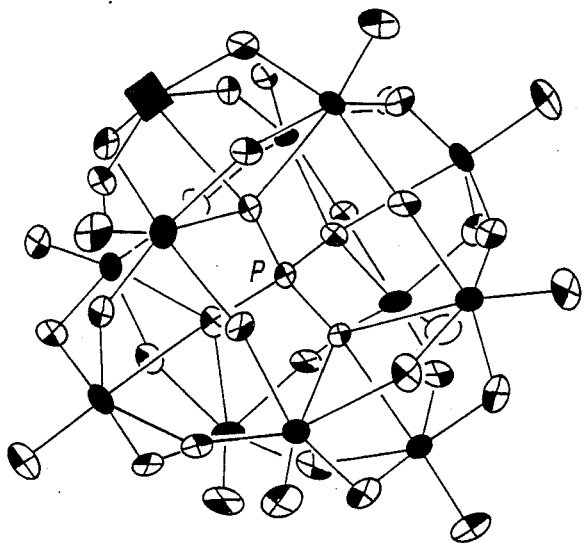
FIG. 1 illustrates the molecular structure of an exemplary transition metal-substituted polyoxometalate of the present invention, Co$^{II}$PW$_{11}$O$_{39}$$^{5-}$. (Solid circles=W atoms; hatched circles=O atoms; P atom marked; and square=transition metal.)

The process of this invention is based on the inventor's discovery that a specific class of transition metal-substituted polyoxometalates possess outstanding catalytic activity in homogeneous catalytic oxidation reactions; carbon-hydrogen bond hydroxylation and alkene epoxidation reactions. The specific class of transition metal-substituted polyoxometalates used in the process of the present invention are characterized by the fact that the transition metal itself (1) is encased or ligated by several oxygen atoms of the metal oxide framework of the polyoxometalate, and (2) that the transition metal itself has at least one coordination site available for coordination to the oxygen donor and/or the organic substrate being oxidized.

The metal-substituted polyoxometalates used in the process of the present invention belong to a very broad class of inorganic materials which include heteropolyacids, heteropolytun states, and related compounds. Many of these compounds are known. Some have been used in catalytic applications. Others have been made for the purpose of academic study only.

The transition metal-substituted polyoxometalates used in the present process have never before been used to promote either a homogeneous catalytic alkane hydroxylation reaction or a homogeneous catalytic epoxidation reaction. The present transition metal-substituted polyoxometalates which have a transition metal (defined below) encased or ligated by several oxygen atoms of the metal oxide framework of the polyoxometalate structure and being further characterized by the fact that this transition metal has at least one coordination site available for coordination to oxygen donors or organic substrates used in the process of the present invention, have never been used in homogeneous oxidation reactions.

Simple polyoxometalates, which do not have the critical transition metal found in the catalyst of the present invention, have been known for over a century. For example, there exists three primary types of polyoxometalates. The first polyoxometalate typically possesses a central atom which can be a phosphorus atom, a silicon atom, a germanium atom, an arsenic atom, etc. surrounded by twelve molybdenum, tungsten, and/or vanadium metal ions and forty oxygen atoms. These molecules have the Keggin structure. The second polyoxometalate possesses two central phosphorus, etc. atoms surrounded by a total of eighteen molybdenum, tungsten, or vanadium metal ions and sixty-two oxygen atoms. The third polyoxometalate possesses five central phosphorus atoms surrounded by thirty molybdenum, tungsten, or vanadium metal ions and one hundred and ten oxygen atoms.

Some of these simple polyoxometalates (i.e., those with the Keggin structure) have been used in homogeneous and heterogeneous catalysis. For examples of their use in heterogeneous catalysis, see the following publications:

(1) McMonagle, J. B.; Moffat, J. B. "The Catalysis of Methanol and Ethanol Conversion on Mn and W Heteropolycompounds" *J. Catal.* 1985, 91,132;

(2) Akimoto, M.; Ikeda,, H.; Okabe, A.; Echigoya, E. "12-Heteropolymolybdates as Catalysts for Vapor-Phase Oxidative Dehydrogenation of Isobutyric Acid" *J. Catal.* 1984, 89, 196;

(3) Hayashi, H.; Moffat, J. B.; "Conversion of Methanol into Hydrocarbons over Ammonium 12-Tungstophosphate" *J. Catal.* 1983, 83, 192;

(4) Baba, T.; Sakai, J.; Ono, Y. "The Conversion of Methanol into Hydrocarbons over Metal Salts of Heteropolyacids" *Bull. Chem. Soc. Japan* 1982, 55, 2657;

(5) Baba, T.; Sakai, J.; Watanabe, H.; Ono, Y. "The Conversion of Methanol in Hydrocarbons over Dodecatungstophosphoric Acid" *Bull. Chem. Soc. Japan* 1982, 55, 2555;

(6) Konishi, Y.; Sakata, K.; Misono, M.; Yoneda, Y. "Catalysis By Heteropoly Compounds. IV Oxidation of Methacrolein to Methacrylic Acid over 12Molybdophosphoric Acid" *J. Catal.* 1982, 77, 169;

(7) Akimoto, M.; Tsuchida, Y.; Sato, K.; Echigoya, E. "12-Heteropolymolybdates as Catalysts for Vapor-Phase Oxidative Dehydrogenation of Isobutyric Acid" *J. Catal.* 1981, 72, 83;

(8) Ai, M. "Characteristics of Heteropoly Compounds as Catalysis for Selective Oxidation" J. Catal. 1981, 71, 88.

As discussed in the above publications, the principal polyoxometalates used in heterogeneous catalysis are the heteropoly compounds with either H+ (the heteropoly acids) or other inorganic cations (e.g. $Na^+$, $K^+$, $Ca^{2+}$, etc.) as the counterion. Most of the heterogeneous catalysis using polyoxometalates involves the use of elevated temperatures (250° to more than 350° C.), the polyoxometalates in the solid phase and the reactants in the gas phase.

In homogeneous catalysis, heteropolyacids have been used in (a) the oxidation of sulfur compounds, (b) the bromination of aromatic compounds, (c) the oxidation of hydrocarbons, and (d) the epoxidation of olefins by aromatic hydroperoxides. (See Kozhevnikov et al., *Russian Chemical Reviews,* 51 (11), 1982, pp. 1075–1088.) The present catalysts compare to those cited in the Russian Chem. Rev. article as follows.

The polyoxometalates cited in the above *Russian Chemical Reviews* article are regular polyoxometalates. That is, they contain only d° cations (e.g., $Mo^{VI}$, $W^{VI}$, or $V^V$). They are completely inactive as oxygen transfer catalysts at 25° C. with some oxygen donors, including the iodosylarenes. In general, under conditions ideally suited for their use as catalysts they are far less active as catalysts than the transition metal-substituted polyoxometalates.

No transition metal-substituted polyoxometalates in which the transition metal contains at least one d-orbital electron have been used in homogeneous catalytic oxidations. As should be noted, in the transition metal-substituted polyoxometalates of the present invention, the transition metal (defined infra) possess at least one d-orbital electron.

Some polyoxometalates contain transition metals used in the present catalysts, where the transition is buried with the molecular framework, have been reported. These polyoxometalates and the heteropolyacids disclosed by Kozhevnikov et al. are however both fundamentally different structurally from the catalysts used in this invention because they do not contain the key transition metal ligated by the oxygen atoms of the metal oxide framework of the molecule and which has a coordination site available to the oxygen donor and-/or substrate. If they contain one of the transition metals used in the catalysts of this invention, this transition metal is situated in the center of the polyoxometalate structure. These compounds are accordingly fundamentally different structurally from the transition metal-substituted polyoxometalates used in this invention in which the transition metal is situated at a surface site of the polyoxometalate structure. This surface site situated transition metal provides the high homogeneous catalytic oxidation activity which distinguish the present transition metal-substituted polyoxometalates over all other polyoxometalates and related compounds.

Polyoxometalate supported organometallic complexes are also known. These are discussed, for example, by Finke et al. in *J. Am. Chem. Soc.,* 1981, 103, 1587–1589. These polyoxometalate supported organometallic complexes are also distinct from the transition metal-substituted polyoxometalates used in the present invention. Polyoxometalate supported organometallic complexes (PSOC hereinafter) in most if not all cases contain an organometallic center, that is a metal fragment that contains at least one carbon-metal bond. The organometallic moiety is usually appended to the exterior of the polyoxometalate skeleton. By contrast, the transition metal-substituted polyoxometalates used in the present invention do not contain organometallic groups and do not contain moieties appended to the exterior of the polyoxometalate. Rather they have substitutional atoms within the polyoxometalate skeleton, resulting in a structure that is minimally changed from the parent polyoxometalate.

The PSOC's are also very air sensitive, making them essentially useless in oxidation reactions. By contrast the transition metal-substituted polyoxometalates used in the present invention are completely stable in air, making their use in oxidation reactions not only possible, but very advantageous.

In this document the term "transition metal" is given a very specific meaning and is defined as being a member selected from the group consisting of chromium, manganese, iron, cobalt, nickel, copper, technetium, rubidium, rhodium, palladium, silver, rhenium, and iridium. Of these transition metals, chromium, manganese, iron, cobalt, nickel and copper, are preferably used in the present catalysts. Manganese, cobalt, chromium and copper are most preferably used in the present catalysts.

The transition metal-substituted polyoxometalates used in the process of this invention are characterized by the fact that the transition metal, also identified by variable (M), is situated at a molecular surface site of the polyoxometalate as illustrated in the FIGURE which illustrates the surface site occupancy of the cobalt atom of $Co^{II}PW_{11}O_{39}{}^{5-}$. In essence, the transition metal-substituted polyoxometalates used in the present invention are transition metal reconstituted defect or "lacunary" polyoxometalates. In addition, the transition metal must have at least one coordination site available for coordination with the oxygen donors and/or substrates used in the present invention.

Thus, in general the transition metal-substituted polyoxometalates used in the present invention are characterized by containing one of the transition metals, defined above, encased or ligated by several oxygen atoms which make up the metal oxide framework of the polyoxometalate structure. This transition metal is situated on the molecular surface site so as to permit the transition metal to have at least one coordination site available for coordination to the oxygen donors and/or organic substrates used in the present invention.

More specifically, however, transition metal-substituted polyoxometalates used in the process of the present invention are compounds having one of the following general formulae:

$$[(M)XW_xMo_yV_zO_{39}]Q_aH_bLi_c \quad ; \text{(i) wherein}$$

$x+y+z=12$; or $$[(M)X_2W_lMo_mV_nO_{61}]Q_dH_eLi_f \quad ; \text{(ii) wherein}$$

$l+m+n=18$; or $$[(M)X_5W_pMo_qV_rO_{109}]Q_gH_hLi_i \quad ; \text{(iii) wherein}$$

In formulae (i) to (iii) above, the values of $(a+b+c)$ or of $(d+e+f)$ or of $(g\ h+i)$ add up to the charge on the transition metal-substituted polyoxometalate. This charge is well known to one skilled in the art and depends on the numbers of the tungsten, molybdenum, and vanadium atoms present in any one structure.

Variable (M) is of course one of the transition metals defined supra in this document. Variable X is a "heteroatom" buried in the structure of the transition metal-substituted polyoxometalate. That is, X does not have a coordination site available for coordination with either the oxygen donor or the solvent used in the process of this invention. X can be many different nonmetal ions, for example X can be a phosphorus atom, an arsenic atom, a silicon atom, a germanium atom, a boron atom, an aluminum atom, etc. or a zinc (II) ion, or any of many transition metal ions, for example cobalt (II), cobalt (III), iron (III), etc.

Variable Q is a group $R_4{}^2N^+$, $R_4{}^2P^+$, or $R_4{}^2As^+$, wherein any group $R^2$ in the molecule is independently a $C_{1-30}$ alkyl group which may be branched, straight, cyclic, or a combination of these, or $R^2$ is a $C_{6-30}$ aryl group, a $C_{7-30}$ aralkyl group or a $C_{3-30}$ aromatic heterocyclic group where the heteroatom can be S, O, N or P.

Although numerous polyoxometalate and related compounds are known, several novel unknown transition metal-substituted polyoxometalate compounds can be used in the present invention. These include:

$$Q_w{}^1H_{10-w}[Co_4P_2W_{18}O_{68}]\cdot\mu H_2O \quad \text{(iv)}$$

$$Q_w{}^1H_{10-w}[Cu_4P_wW_{18}O_{68}]\cdot\mu H_2O \quad \text{(v)}$$

$$Q_w{}^1H_{10-w}[Mn_4P_2W_{18}O_{68}]\cdot\mu H_2O \quad \text{(vi)}$$

$$Q_2{}^1H_{10-w}[Fe_4P_2W_{18}O_{68}]\cdot\mu H_2O \quad \text{(vii)}$$

where $Q^1$ for all the above is tetra-n-hexyl ammonium, tetra-n-pentyl ammonium, or any quaternary salt $R_4{}^3N^+$, $R_4{}^3P^+$, or $R^3As^+$, where each $R^3$ is independently a $C_{1-30}$ alkyl, a $C_{6-30}$ aryl, or a $C_{7-30}$ aralkyl, and wherein at least one $R^3$ in a molecule $Q^1$ is a $C_{8-30}$ alkyl when all other $R^3$ are $C_{1-30}$ alkyl and when $Q^1$ is $R_4{}^3N^+$. $R^3$ is either straight chain or branched or cyclic, unsaturated, saturated, aromatic, or a combination thereof. Also any combination of the above counterions $Q^{(1)+}$ or $H^+$ can be exchanged with lithium $(Li^+)$ such that the total number of ions remains 10. (In this case, and in other places throughout this text $Q^g$ will be synonymous with $Q^{(g)+}$, where g is an integer.) In formulae (iv) to (vii) variable w is an integer of from 0 to 10.

In all of the formulae in this document, is the number of $H_2O$ molecules present per molecule of complex. This number is variable depending on recrystallizing conditions, etc., and may be 0 to 50.

All of the following transition metal-substituted polyoxometalates (viii to xi) which can be used in this invention are also novel. In these compounds $Q^2$ is a quaternary salt or $R_4{}^4N^+$, $R_4{}^4P^+$ or $R_4{}^4As^+$, where each $R^4$ is independently a $C_{1-30}$ alkyl group, a $C_{6-30}$ aryl group, or a $C_{7-30}$ aralkyl group, where each group can be, independently, straight chained or branched, or cyclic, or a combination thereof, with the further proviso that at least one group $R^4$ is a $C_{8-30}$ alkyl when all other groups $R^4$ in a molecule $Q^2$ are $C_{1-30}$ alkyl and $Q^2$ is $R_4{}^4N^+$. Also, as for the class of compounds above, any combination of the counterions $Q^{((2)+}$ or $H+$ can be exchanged with lithium $(Li^+)$ such that the total number of ions remains 16. In formulae (viii) to (xi), variable w is an integer from 0 to 16.

$$Q_w{}^2H_{16-w}[Co_4P_4W_{30}O_{112}]\cdot\mu H_2O \quad \text{(viii)}$$

$$Q_w{}^2H_{16-w}[Cu_4P_4W_{30}O_{112}]\cdot\mu H_2O \quad \text{(ix)}$$

$$Q_w{}^2H_{16-w}[Mn_4P_4W_{30}O_{112}]\cdot\mu H_2O \quad \text{(x)}$$

$$Q_w{}^2H_{16-w}[Fe_4P_4W_{30}O_{112}]\cdot\mu H_2O \quad \text{(xi)}$$

The following transition metal-substituted polyoxometalates (xii) which can be used in this invention are also novel. In these compounds $Q^3$ is a quaternary salt, $R_4{}^5N^+$, $R_4{}^5P^+$ or $R_4{}^5As^+$, where $R^5$ is independently a $C_{1-30}$ alkyl group, a $C_{6-30}$ aryl group or a $C_{7-30}$ aralkyl group, wherein at least one group $R^5$ is a $C_{8-30}$ alkyl when all groups $R^5$ in a molecule $Q^3$ are $C_{1-30}$ alkyl and $Q^3$ is $R^5N+$Straight chain, branched or cyclic alkyl groups can be used for those groups $R^5$. Also, as for the classes of compounds above, any combination of the counterions $)Q^{(3)+}$ or $H^+$ can be exchanged with lithium $(Li^+)$ such that the total number of ions remains 8 for the following species.

$$Q_w{}^3H_{8-w}Si_2NbW_{18}O_{77}]\cdot H_2O \quad \text{(xii)}$$

The following transition metal-substituted polyoxometalates (xiii) which can also be used in this invention are also novel. In these compounds $Q^4$ is a quaternary salt, $R_4{}^6N^+$, $R_4{}^6P+$, or $R_4{}^6As^+$, where $R^6$ is a $C_{1-30}$ alkyl group, a $C_{6-30}$ aryl group or a $C_{7-30}$ aralkyl group. Straight chain, branched or cyclic groups can be used for those groups $R^6$. Also, as for the classes of compounds above, any combination of the counterions Qhd w(4)+ or H+ can be exchanged with lithium (Li+) such that the total number of ions remains 12 for the following species.

$$Q_w{}^4H_{12-w}[(M)_3P_2W_{18}O_{68}]\cdot H_2O; \qquad (xiii)$$

where (M)=$Co^{II}$, $Mn^{II}$, $Cu^{II}$, or $Fe^{II}$.

The transition metal-substituted polyoxometalates of the present invention can be made in accordance with the following general description. The parent heteropolyacid of tungsten or molybdenum is dissolved in water and the pH adjusted until the appropriate defect or "lacunary" structure, as is well known in the art, becomes the thermodynamically predominant form. For example, the preparation of $PW_{11}O_{39}{}^{7-}$ is effected by adjusting an aqueous solution of $H_3PW_{12}O_{40}$ to a pH of 6 with lithium carbonate or another such base. These reactions can be monitored very quantitatively by $^{183}W$ NMR spectroscopy.

This defect or "lacunary" structure needs not be isolated but can be treated immediately with an aqueous solution of an appropriate transition metal salt. Any common aquated water-soluble salt will suffice. For example, an aqueous solution of the hydrated $Co^{II}$ chloride can be used. Upon mixing the transition metal ion with the defect polyoxometalate, the transition metal is incorporated into the defect site reconstituting the approximate structure of the parent polyoxometalate with the transition metal ion taking the place of one of the original tungsten ions.

Continuing with the example above, $PW_{11}O_{39}{}^{7-}$ reacts with MnII to form $(MnII)PW_{11}O_{39}{}^{5-}$. The rate of incorporation of the transition metal into the defect structure depends on the d orbital occupancy of the transition metal. Reactions of defect polyoxometalates with $Co^{II}$ and $Mn^{II}$, for example, are instantaneous at 25° C., while reaction with $Cr^{III}$ is slow. The transition metal substituted polyoxometalate is then precipitated from the aqueous solution by addition of a desired organic cation and the resulting salt is recrystallized from an appropriate organic solvent. Often acetonitrile proves satisfactory.

Exemplary preparations for the defect or "lacunary" polyoxometalates and their reconstitution with transition metal ions are given in the publications referenced below.

(1) Massart, R.; Constant, R.; Fruchart, J.-M.; Ciabrini, J.-P. Fournier, M. *Inorg. Chem.* 1977, 16, 2916;

(2) Tourne, C. C. R. *Acad. Sc. Paris, Ser C*, 1968, 702;

(3) Tourne, C.M.; Tourne, G. F.; Malik, S. A.; Weakley, T.J.R. *J. Inorg. Nucl. Chem.* 1970, 32, 3875;

(4) Tourne, C.; Tourne, G. *Bull. Soc. Chim. France* 1969, 1124;

(5) Malik, S. A.; Weakley, T. J. R. *J. Chem. Soc. (A)*, 1968, 2647; or (6) Zonnevijlle, F.; Tourne, C.M.; Tourne, G. E. *Inorg. Chem.* 1982, 21, 2742, and 1983, 22, 1198.

Without desiring to limit the scope of this invention, it is currently understood that the group Q (including $Q^1$, $Q^2$, etc. ...) should advantageously possess those qualities necessary to provide the transition metal-substituted polyoxometalates sufficient solubility in the reaction mixture to permit a homogeneous catalytic process to proceed. Thus if a solvent of very low polarity is desired, a cation Q (including $Q^1$, $Q^2$, etc. ...) having a low polarity should be used. By contrast, if a polar solvent is desired, a cation Q (including $Q^1$, $Q^2$, etc. ...) having a higher polarity should be used.

Although solvation of the transition metal-substituted polyoxometalate catalyst used in the present invention is advantageous, it is by no means required that all of the transition metal-substituted polyoxometalate material be completely dissolved in the reaction medium. Under certain reaction conditions, it is quite possible that some transition metal-substituted polyoxometalate material remains unsolvated without adversely affecting the process of the present invention.

For that matter, although this is a homogeneous process, it is by no means required that all components form an absolutely perfect homogeneous blend. For example, solubility between different oxygen donors varies in some of the reactions which are part of the present invention, and the process of the present invention can be advantageously run with some of its components not completely dissolved in the reaction medium.

The organic substrates which can be oxidized with the process of the present invention are all organic substrates which are susceptible to carbon-hydrogen bond hydroxylation reactions and/or epoxidation reactions. These substrates are characterized by the fact that they all possess either a carbon-hydrogen bond or an olefinic functionality. Substrates susceptible to both epoxidation and carbon-hydrogen bond hydroxylation reactions can of course be used.

As anyone skilled in this art will recognize, the class of organic substrates which can be oxidized with the process of the present invention is very broad. These organic substrates can be gaseous liquid, or solid at room temperature. They can be aliphatic, they can be unsaturated or polyunsaturated, they can be aromatic, they can contain heteroatoms, they can be cyclic, they can be linear, they can be branched, they can possess other functional groups, or they can contain a combination of these characteristics.

The organic substrates which can be oxidized in accordance with the process of the present invention can, for example, contain from 1 to over 100 carbon atoms in the case of the alkane hydroxylation reactions, and from 2 to over 100 carbon atoms for the epoxidation reactions. Thus $C_{1-100}$ alkanes which may be linear, branched, cyclized can be used. Similarly, corresponding $C_{2-100}$ alkenes and alkynes can be used. $C_{6-100}$ arenes, aralkenes, heterocyclic compounds, esters, ethers, ketones, aldehydes, nitriles, carboxylic acids, nitro compounds and many other classes of organic compounds can be oxidized. The organic substrates also includes amines, thiols, sulfides, disulfides and related compounds of Se or Te, or phosphines, or phosphites and related compounds of As and Sb.

For example, this organic substrate can be a straight $C_{1-100}$ alkane, a branched $C_{4-100}$ alkane, a cyclic $C_{3-100}$ alkane, a $C_{1-100}$ haloalkane, a $C_{4-100}$ branched haloalkane, a $C_{3-100}$ halocyclic alkanes, a linear $C_{2-100}$ alkene, a branched $C_{4-100}$ alkene, a cyclic $C_{4-100}$ alkene, a $C_{6-100}$ arene, $C_{7-100}$ aralkane, a $C_{3-100}$ heterocyclic compound containing at least one oxygen atom or at least one sulfur atom or at least one nitrogen atom or at least one phosphorus atom, a $C_{2-100}$ ester, a $C_{2-100}$ ether, a $C_{3-100}$ ketone, $C_{1-100}$ aldehyde, $C_{2-100}$ nitrile, a $C_{1-100}$ carboxylic acid, a $C_{1-100}$ nitro compound, a $C_{1-100}$ ammonium salt, $C_{1-100}$ thiol, a $C_{2-100}$ sulfide, a $C_{2-100}$ disulfide, a $C_{1-100}$ phosphine, a $C_{1-100}$ phosphine oxide, a $C_{3-100}$ phosphite, a $C_{3-100}$ phosphate or an arsenic or antimony analog of the said phosphine, phosphites, or their oxides.

With organic substrates possessing amine, thiol, sulfide, disulfide, and related Se or Te compounds, phosphines, phosphites and related As and Sb compounds, the catalytic oxidation process of the present invention will in many cases promote the concomitant oxidation of the heteroatom. This can be prevented by adjusting the pH of the catalytic oxidation reaction to a pH at which the heteroatom is protonated. Alternatively, if no disadvantage is to be suffered by obtaining an oxidized heteroatom, the catalytic oxidation process can be carried out and one obtains an organic substrate in which the heteroatom has been hydrogen bond hydroxylation and/or epoxidation reaction.

In one embodiment of this invention, the carbon-hydrogen bond (e.g., alkane) hydroxylation product, which is an alcohol, can be allowed to further react with the catalysts and the oxygen donor to provide the corresponding carbonyl-containing molecule. Thus one can either allow the oxidation reaction to proceed only to the level of oxidizing the carbon-hydrogen bond to the corresponding hydroxyl functionality. Or, if desired, one can allow this reaction to proceed further to obtain the corresponding or aldehyde. Tertiary carbon-hydrogen bonds, of course, are oxidized only to the corresponding hydroxyl functionality.

Typical oxygen donors useful in the present invention include $C_{1-30}$ alkyl hydroperoxides, which can be unsubstituted or substituted (including the commercially available t-butylhydroperoxide, TBHP, and cumylhydroperoxide), hydrogen peroxide, $C_{6-30}$ iodosylarenes which can be unsubstituted or substituted, $C_{1-30}$ amine N-oxides which can be unsubstituted or substituted, $C_{1-30}$ peracids which can be unsubstituted or substituted, hypochlorites, and other halogen oxyanions, oxaziridines (e.g., 2-phenylsulfonyl-3-(p-nitrophenyl)oxaziridine), and highly oxidizing transition metal oxo compounds such as chromate, dichromate, permanganate, ruthenium and osmium tetroxides. The substituents which can be used on these oxygen donors include $C_{1-30}$ alkyl, halogen atoms (i.e., fluorine, chlorine or bromine), nitro, cyano, hydroxyl, $C_{1-30}$ alkoxy, etc. . . . substituents.

The oxygen donor is used in an amount sufficient to effectuate the desired level of oxidation of the substrate. Thus, about an amount of oxygen donor equivalent to the amount of substrate, on a molar basis, can be used if monooxidation is desired. An excess of oxygen donor relative to substrate can also be used and this generally results in the polyhydroxylation and/or polyepoxidation of the substrate (i.e., the hydroxylation of a number of carbon-hydrogen bonds and/or the epoxidation of a number of olefinic functionalities per substrate molecule). Additional oxygen donor over that theoretically required to completely oxidize the substrate can be used with substrates difficult to oxide to increase yields of oxidation products. Of course, a theoretically inferior amount of oxygen donor relative to substrate can be used if one wishes oxidation of only part of the substrate. Combinations of two or more different oxygen donors can be used. The oxygen donor and substrates can be used in molar ratios which can range from 1:10,000 to 10,000:1, preferably about 10:1 to 1:10, based on the desired level of oxidation of the substrate.

Although the oxidation process of the present invention does not require the use of a solvent, a solvent can be used. Any organic liquid or water can be used as a solvent provided that the solvent does not oxidize more rapidly than the desired substrate, and further provided that the catalyst, oxygen donor, and substrates be sufficiently soluble in the solvent. As discussed above, the catalytic reactions of course do not need to be 100% homogeneous. Exemplary solvents include acetonitrile, hexamethylphosphoramide, halogenated solvents (e.g., halogenated aromatics, dichloromethane and dichloroethane), aromatics (e.g., toluene, xylenes and benzene) ethers, (e.g., diethyl ether and tetrahydrofuran), and mixtures thereof. In short, essentially any solvent can be used except that (1) with pure alkanes there may be solubility problems, (2) with readily oxidizable solvents (e.g., DMSO), the solvent can compete with the substrate, and (3) with basic functionality-containing solvents (e.g., amines), some catalyst damage can be observed.

The homogeneous catalytic oxidation reaction of the present invention is preferably run in the liquid phase where the substrate and the oxygen donor can be a solid, a liquid, or a gas dissolved in the liquid reaction medium. Accordingly a reaction temperature sufficient to permit the oxidation reaction to proceed at an appropriate rate and below the point at which the reaction mixture would be in the gas phase is used. Usable temperatures will accordingly vary as a function of the solvent used, the catalyst used, the oxygen donor used, the substrate oxidized, and the concentrations of reactants used. Typical ranges of temperatures include $-30°$ C. to $300°$ C., preferably $0°$ to $150°$ C., and most preferably $25°$ to $100°$ C.

Other features of the invention will become apparent in the course of the following descriptions of exemplary embodiments which are given for illustration of the invention and are not intended to be limiting thereof.

EXPERIMENTAL SECTION

Alkane hydroxylations:

Catalysts used in the present invention were prepared by obtaining a $H_3PW_{12}O_{40}$ starting material by following Wu's procedure published in *J. Biol. Chem. Vol.* 43, pp 189 (1920). This $H_3PW_{12}O_{40}$ was used to prepare the transition metal-substituted polyoxometalates used in the present invention by following the procedure of Domaille published in *J. Am. Chem. Soc.* (1984) Vol. 106, pp. 7677 and that of Tourne et al. published in *J. Inorg. and Nucl. Chem.* (1970) Vol. 32, pp. 3875. Thus the transition metal-substituted polyoxometalates of the present invention were obtained by substituting the $VSO_4$ used in these references with $Mn(NO_3)_2$, $Co(NO_3)_2$, $KCr(SO_4)_2$ or $FeSO_4$. The transition metal-substituted polyoxometalates were then stored in a sealed vial until used.

Iodosylbenzene (PhIO) was obtained by following the procedure of Lucas et al. published in "Organic Synthesis" published in "Organic Synthesis" published by Wiley, New York (1955), collected Volume 3, page 483. Pentafluoroiodosylbenzene (PFIB) was obtained by following the procedure of Schmeisser et al. in *Chem. Ber.*, Vol. 100, pp. 1633 (1967). Tert-butylhydroperoxide (TBHP) was obtained commercially from Aldrich Chemical Company and used without further purification.

The substrates were obtained commercially. High purity commercial substrates were obtained, these were used without further purification. If it was desired to increase their level of purity, standard literature methods were used.

Experiment No. 1

A 25 ml degassed and Ar-filled Schlenk flask was charged with 0.012 mmole (ca. 50 mg.) of $(MnPW_{11}O_{39})(H)NBu_4)_4$ in 5 ml of acetonitrile and 0.6 ml of cyclohexane. At 65° C. and under stirring, 20 μl (0.18 mmole) of tert-butylhydroperoxide was added to initiate the reaction.

After 24 hours, the reaction was interrupted and a GC analysis of the reaction mixture indicated a combined 27% yield of cyclohexanol and cyclohexanone (% yields based on the amount of tert-butylhydroperoxide used).

Experiment No. 2

A 25 ml degassed and Ar-filled Schlenk flask was charged with 0.012 mmole (ca. 50 mg) of $(CrPW_{11}O_{39})NBu_4)_4$ in 5 ml of acetonitrile and 0.6 ml of cyclohexane. At 65° C. and under stirring, 20 μl (0.18 mmole) of tert-butylhydroperoxide was added to initiate the reaction.

After 24 hours the reaction was interrupted and a GC analysis of the reaction mixture indicated a combined 26% yield of cyclohexanol and cyclohexanone (% yields based on the amount of tert-butylhydroperoxide used).

Experiment No. 3

A 25 ml degassed and Ar-filled Schlenk flask was charged with 0.012 mmole (ca. 50 mg) of $(CuPW_{11}O_{39})(H)NBu_4)_4$ in 5 ml of acetonitrile and 0.6 ml of cyclohexane. At 65° C. and under stirring, 20 μl (0.18 mmole) of tert-butylhydroperoxide was added to initiate the reaction.

After 24 hours the reaction was interrupted and a GC analysis of the reaction mixture indicated a combined 26% yield of cyclohexanol and cyclohexanone (% yields based on the amount of tert-butylhydroperoxide used).

Experiment No. 4

A 25 ml degassed and Ar-filled Schlenk flask was charged with 0.012 mmole (ca. 50 mg) of $(CoPW_{11}O_{39})(H)NBu_4)_4$ in 5 ml of acetonitrile and 0.6 ml of cyclohexane. At 65° C. and under stirring, 20 μl (0.18 mmole) of tert-butylhydroperoxide was added to initiate the reaction.

After 24 hours the reaction was interrupted and a GC analysis of the reaction mixture indicated a combined 25% yield of cyclohexanol and cyclohexanone (% yields based on the amount of tert-butylhydroperoxide used).

TABLE 1

| Exp. No. | substrate | oxygen donor | yield* of cyclohexanol + cyclohexanone* |
|---|---|---|---|
| 1 | $(MnPW_{11}O_{39})(H)(NBu_4)_4$ | t-butylhydroperoxide | 27% |
| 2 | $(CrPW_{11}O_{39})(NBu_4)_4$ | t-butylhydroperoxide | 26 |
| 3 | $(CuPW_{11}O_{39})(H)(NBu_4)_4$ | t-butylhydroperoxide | 26 |
| 4 | $(CoPW_{11}O_{39})(H)(NBu_4)_4$ | t-butylhydroperoxide | 25 |

*yields based on amount of t-butylhydroperoxide used.

Experiment No 5

A degassed and Ar-filled Schlenk flask (25 ml) was charged with 0.5 ml of cyclohexane and $1.5 \times 10^{-5}$ mole $(MnPW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 46% yield of cyclohexanol and a 37% yield of cyclohexanone (% yields based on amount of catalyst used).

Experiment No 6

A degassed and Ar-filled Schlenk flask (25 ml) was charged with 0.5 ml of cyclohexane and $1.5 \times 10^{-5}$ mole $(MnPW_{11}O_{39})(H)NBu_4)_4$ dissolved in 5 ml of $CH_3CN$. At 25° C., $1.5 \times 10^{-4}$ mole of pentafluoroiodosylbenzene (oxygen donor) was added. The reaction mixture was degassed and stirred under Ar at 25° C. for an additional 3 hrs.

GC analysis of the reaction mixture indicated a 38% yield of cyclohexanol and a 17% yield of cyclohexanone (% yields based on amount of catalyst used).

Experiment No 7

A degassed and Ar-filled Schlenk flask (25 ml) was charged with 0.5 ml of cyclohexane and $1.5 \times 10^{-5}$ mole $(CoPW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 26% yield of cyclohexanol and a 10% yield of cyclohexanone (% yields based on amount of catalyst used).

Experiment No 8

A degassed and Ar-filled Schlenk flask (25 ml) was charged with 0.5 ml of cyclohexane and $1.5 \times 10^{-5}$ mole $(CoPW_{11}O_{39})(H)NBu_4)_4$ dissolved in 5 ml of $CH_3CN$. At 25° C., $1.5 \times 10^{-4}$ mole of pentafluoroiodosylbenzene (oxygen donor) was added. The reaction mixture was then degassed and stirred under Ar at 25° C. for an additional 3 hrs.

GC analysis of the reaction mixture indicated a 24% yield of cyclohexanol and a 9% yield of cyclohexanone (% yields based on amount of catalyst used).

Experiment No 9

A degassed and Ar-filled Schlenk flask (25 ml) was charged with 0.5 ml of 2,3-dimethylbutane and $1.5 \times 10^{-5}$ mole $(MnPW_{11}O_{39})(H)NBu_4)_4$ dissolved in 5 ml of $CH_3CN$ At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 84% yield of 2-hydroxy-2,3-dimethylbutane and a <1% yield of 1-hydroxy-2,3-dimethylbutane (% yields based on amount of catalyst used).

Experiment No 10

A degassed and Ar-filled Schlenk flask (25 ml) was charged with 0.5 ml of 2,3-dimethylbutane and $1.5 \times 10^{-5}$ mole $(MnPW_{11}O_{39})(H)NBu_4)_4$ dissolved in 5 ml of $CH_3CN$. At 25° C., $1.5 \times 10^{-4}$ mole of pentfluoroiodosylbenzene (oxygen donor) was added. The reaction mixture was then degassed and stirred under Ar at 25° C. for an additional 3 hrs.

GC analysis of the reaction mixture indicated a 40% yield of 2-hydroxy-2,3-dimethylbutane and a <1% yield of 1-hydroxy-2,3-dimethylbutane (% yields based on amount of catalyst used).

Experiment No 11

A degassed and Ar-filled Schlenk flask (25 ml) was charged with 0.5 ml of 2,3-dimethybutane and $1.5 \times 10^{-5}$ mole $(CoPW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 24% yield of 2-hydroxy-2,3-dimethylbutane and a <1% yield of 1-hydroxy-2,3-dimethylbutane (% yields based on amount of catalyst used).

Experiment No 12

A degassed and Ar-filled Schlenk flask (25 ml) was charged with 0.5 ml of 2,3-dimethylbutane and $1.5 \times 10^{-5}$ mole $(CoPW_{11}O_{39})(H)NBu_4)_4$ dissolved in 5 ml of $CH_3CN$. At 25° C., $1.5 \times 10^{-4}$ mole of pentafluoroiodosylbenzene (oxygen donor) was added. The reaction mixture was then degassed and stirred under Ar at 25° C. for an additional 3 hrs.

GC analysis of the reaction mixture indicated a 7% yield of 2-hydroxy-2,3-dimethylbutane and a <1% yield of 1-hydroxy-2,3-dimethylbutane (% yields based on amount of catalyst used).

Experiment No 13

A degassed and Ar-filled Schlenk flask (25 ml) was charged with 0.5 ml of 1,2,3,4-tetrahydronaphthalene and $1.5 \times 10^{-5}$ mole $(MnPW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 459% yield of 1,2,3,4-tetrahydro-1-naphthol and a 78% yield of tetralone (% yields based on amount of catalyst used).

Experiment No 14

A degassed and Ar-filled Schlenk flask (25 ml) was charged with 0.5 ml of 1,2,3,4-tetrahydronaphthalene and $1.5 \times 10^{-5}$ mole $(CoPW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 216% yield of 1,2,3,4-tetrahydro-1-naphthol and a 45% yield of tetralone (% yields based on amount of catalyst used).

Experiment No 15

A degassed and Ar-filled Schlenk flask (25 ml) was charged with 0.5 ml of 1,2,3,4-tetrahydronaphthalene and $1.5 \times 10^{-5}$ mole $(FePW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 186% yield of 1,2,3,4-tetrahydro-1-naphthol and a 115% yield of tetralone (% yields based on amount of catalyst used).

Experiment No 16

A degassed and Ar-filled Schlenk flask (25 ml) was charged with 0.5 ml of 1,2,3,4-tetrahydronaphthalene and $1.5 \times 10^{-5}$ mole $(CrPW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 160% yield of 1,2,3,4-tetrahydro-1-naphthol and a 184% yield of tetralone (% yields based on amount of catalyst used).

Experiment No 17

A degassed and Ar-filled Schlenk flask (25 ml) was charged with 0.5 ml of norbornane and $1.5 \times 10^{-5}$ mole $(MnPW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 10% yield of norborneol and a 1% yield of norcamphor (% yields based on amount of catalyst used).

Experiment No 18

A degassed and Ar-filled Schlenk flask (25 ml) was charged with 0.5 ml of norbornane and $1.5 \times 10^{-5}$ mole $(CoPW_{11}O_{39})(H)NBu_4)_4$ dissolved in 5 ml of $CH_3CN$. At 25° C., $1.5 \times 10^{-4}$ mole of iodosylbenzene (oxygen donor) was added. The reaction mixture was then degassed and stirred under Ar at 25° C. for an additional 3 hrs.

GC analysis of the reaction mixture indicated a 3% yield of norborneol and a 1% yield of norcamphor (% yields based on amount of catalyst used).

TABLE II

| Exp. No. | Substrate | Catalyst | Oxygen Donor | Product (yield)* |
|---|---|---|---|---|
| 5 | cyclohexane | $(MnPW_{11})_{39})^{5-}$ | iodosylbenzene | cyclohexanol (46%) cyclohexanone (37%) |
| 6 | cyclohexane | $(MnPW_{11}O_{39})^{5-}$ | pentafluoro-iodosylbenzene | cyclohexanol (38%) cyclohexanone (17%) |
| 7 | cyclohexane | $(CoPW_{11}O_{39})^{5-}$ | iodosylbenzene | cyclohexanol (26%) cyclohexanone (10%) |
| 8 | cyclohexane | $(CoPW_{11}O_{39})^{5-}$ | pentafluoro-iodosylbenzene | cyclohexanol (24%) cyclohexanone (9%) |
| 9 | 2,3-dimethyl- | $(MnPW_{11}O_{39})^{5-}$ | iodosylbenzene | 2-hydroxy-2,3- |

TABLE II-continued

| Exp. No. | Substrate | Catalyst | Oxygen Donor | Product (yield)* |
|---|---|---|---|---|
| | butane | | | dimethylbutane (84%)<br>1-hydroxy-2,3-dimethylbutane (<1%) |
| 10 | 2,3-dimethyl-butane | $(MnPW_{11}O_{39})^{5-}$ | pentafluoro-iodosylbenzene | 2-hydroxy-2,3-dimethylbutane (40%)<br>1-hydroxy-2,3-dimethylbutane (<1%) |
| 11 | 2,3-dimethyl-butane | $(CoPW_{11}O_{39})^{5-}$ | iodosylbenzene | 2-hydroxy-2,3-dimethylbutane (24%)<br>1-hydroxy-2,3-dimethylbutane (<1%) |
| 12 | 2,3-dimethyl-butane | $(CoPW_{11}O_{39})^{5-}$ | pentafluoro iodosylbenzene | 2-hydroxy-2,3-dimethylbutane (17%)<br>1-hydroxy-2,3-dimethylbutane (<1%) |
| 13 | 1,2,3,4-tetrahydro-naphthalene | $(MnPW_{11}O_{39})^{5-}$ | iodosylbenzene | 1,2,3,4-tetrahydro-1-naphthol (459%)<br>tetralone (78%) |
| 14 | 1,2,3,4-tetrahydro-naphthalene | $(CoPW_{11}O_{39})^{5-}$ | iodosylbenzene | 1,2,3,4-tetrahydro-1-naphthol (216%)<br>tetralone (45%) |
| 15 | 1,2,3,4-tetrahydro naphthalene | $(FePW_{11}O_{39})^{5-}$ | iodosylbenzene | 1,2,3,4-tetrahydro-1-naphthol (186%)<br>tetralone (115%) |
| 16 | 1,2,3,4-tetrahydro-naphthalene | $(CrPW_{11}O_{39})^{4-}$ | iodosylbenzene | 1,2,3,4-tetrahydro-1-naphthol (160%)<br>tetralone (184%) |
| 17 | norbornane | $(MnPW_{11}O_{39})^{5-}$ | iodosylbenzene | norborneol (10%)<br>norcamphor (1%) |
| 18 | norbornane | $(CoPW_{11}O_{39})^{5-}$ | iodosylbenzene | norborneol (3%)<br>norcamphor (%) |

*Yields based on amount of catalyst used.

Epoxidations:

Transition metal substituted heteropolytungstates of $C_S$ point group symmetry, of which (n-Bu$_4$N)$_4$H(M)PW$_{11}$-O$_{30}$, (M)=transition metal, 1-(M), is an example, were prepared where (M)=Mn$^{II}$ and Co$^{II}$. We found that these transition metal-substituted heteropolytungstates are remarkably effective epoxidation catalysts using iodosylarenes.

We have specifically addressed the homogeneous catalytic epoxidation of olefins by 1-Mn and 1-Co using iodosylbenzene (PhIO) or pentafluoroiodosylbenzene (PFIB) as oxygen donors. The product selectivities, reaction rates, and, most importantly, stabilities for these epoxidations compare very favorably with those for all metalloporphyrin and related systems in the literature. The complexes are not as susceptible to oxidative degradation during epoxidations as metalloporphyrins, and they are also not susceptible to inactivation by aggregation or other effects.

We have examined many epoxidation reactions by iodosylbenzene and pentafluoroiodosylbenzene catalyzed by 1-Co and 1-Mn as well as by metalloporphyrins and metal triflates. A direct comparison can be made between 1-M/PFIB systems and the [tetrakis(2,6-dichlorophenyl) porphinato]iron(III)/PFIB system examined by Traylor et al. *J. Chem. Soc., Chem. Comm.* 1984, 279. Our catalysts exhibited rates and epoxide selectivities which were as high as any metalloporphyrin-based system in the literature and displayed greater stability.

Representative reactions under low to moderate turnover conditions are summarized in Table III; exact reaction conditions are given in the table. The following points pertain to all reactions catalyzed by 1-(M):

(1) No reaction is seen in the absence of either 1-M or oxidant;

(2) Trans-stilbene gives trans-stilbene oxide and benzaldehyde only (6:1 mol ratio); cis-stilbene gives partially isomerized olefin, cis- and trans-epoxides, and benzaldehyde, products compatible with one or more freely rotating radical intermediates;

(3) The selectivity for production of epoxide is higher in the reactions catalyzed by 1-M than in the reactions catalyzed by the metal triflates or metalloporphyrins (>90% for 1-M with all olefins examined);

(4) The rates of epoxidation with pentafluoroiodosylbenzene, chosen as oxygen donor for its reactivity, follow the order (n-Bu$_4$N)$_4$H(Co)PW$_{11}$O$_{39}$ and (n-Bu$_4$N)$_4$H(Mn)PW$_{11}$O$_{39}$ (most reactive)$\geq$ FeTDCPPCl>MTPPCl>M(OTf)$_2$, (M)=FeII or Mn$^{II}$;

(5) Epoxidations catalyzed by (n-Bu$_4$N)$_4$H(M)PW$_{11}$O$_{39}$ continue far longer than for all other systems examined.

Several epoxidations with all the catalysts in Table III and pentafluoroiodosylbenzene were examined under high turnover conditions (10,000 equiv of pentafluoroiodosylbenzene per equiv of catalyst). The stability order of these homogeneous catalysts, monitored by both the spectral properties of the catalysts and the rate of pentafluoroiodosylbenzene uptake with time, was: M(OTf)$_2$ (least stable) MTPPCl, M=Fe$^{III}$ or Mn$^{III}$, <<FeTDCPPCl<1-M, M=Co$^{II}$ or Mn$^{II}$ (most stable). Only the catalysts, 1-(M), appear to be oxidatively stable in the absence of olefin substrate.

TABLE III

Epoxidation of Olefins by Iodosylbenzene (PhIO) and Pentafluoroiodosylbenzene (PFIB) Catalyzed by Transition-Metal-Substituted Heteropolytungstates and Other Transition-Metal-Based Catalysts[a]

| | | A. Cyclohexene oxidation | | | |
| | | Products (Yields, %)[b,c] | | | |
| Catalyst[d] | Oxidant | Cyclohexene Oxide | 2-Cyclohexene-1-ol | 2-cyclohexene-1-one | Aryl Iodide |

TABLE III-continued

Epoxidation of Olefins by Iodosylbenzene (PhIO) and Pentafluoroiodosylbenzene (PFIB) Catalyzed by Transition-Metal-Substituted Heteropolytungstates and Other Transition-Metal-Based Catalysts[a]

| 1-Mn | PhIO | 67 | <1 | 2.5 | 72 |
|---|---|---|---|---|---|
| 1-Mn | PFIB | 41 | 1.1 | 3.0 | 90 |
| Mn(OTf)$_2$ | PhIO | 24 | 1.1 | 1.8 | 68 |
| Mn(OTf)$_2$ | PFIB | 14 | 1.3 | 2.4 | 90 |
| 1-Co | PhIO | 82 | <1 | 2.0 | 76 |
| Co(OTf)$_2$ | PhIO | 17 | 1.2 | 1.4 | 59 |
| 1-Fe | PhIO | | no reaction | | |
| 1-Fe | PFIB | 14 | e | e | 58 |
| MnTPPCl | PhIO | 24 | 6 | 3 | 70 |
| FeTPPCl | PhIO | 50 | 12 | 3 | 98 |
| CoTPPCl | PhIO | e | <2 | e | e |

B. 1-Hexene oxidation

Products (Yields, %)[b,c]

| Catalyst[d] | Oxidant | 1-hexene-oxide | 2-hydroxy-n-hexane | 2-hexan-one | Aryl Iodide |
|---|---|---|---|---|---|
| 1-Mn | PhIO | 58 | <<1 | 3.5 | 81 |
| 1-Mn | PFIB | 55 | <1 | 4 | 96 |
| Mn(OTf)$_2$ | PhIO | 18 | ? | <1 | 77 |
| Mn(OTf)$_2$ | PFIB | 24 | 2 | 10 | 80 |
| FeTPPCl | PhIO | 28 | 9 | 7 | 77 |
| FeTPPCl | PFIB | 11 | 3 | 3 | 90 |
| FeTDCPPCl | PhIO | 65 | ? | 14 | 96 |
| FeTDCPPCl | PFIB | 76 | 5 | 16 | 98 |

C. Norbornene oxidation

Products (Yields, %)[b,c]

| Catalyst[d] | Oxidant | 2,3-epoxy-2-norbornene | 2-norbor-neol | 2-norbor-nanone | Aryl Iodide |
|---|---|---|---|---|---|
| 1-Co | PhIO | 96[f] | e | e | 97 |
| Co(OTf)$_2$ | PhIO | 96[f] | e | e | 60 |

C. Cyclooctene oxidation[g]

Products (Yields, %)[b,c]

| Catalyst[d] | Oxidant | Cyclooctene-oxide | Aryl Iodide |
|---|---|---|---|
| 1-Co | PhIO | 91 | 60 |
| Co(OTf)$_2$ | PhIO | 25 | 54 |

[a]All reactions were run with an olefin:oxidant:catalyst mol ratio of 500:10:1 at 24° C. under nitrogen or argon; solvent for metalloporphyrin reactions was CH$_2$Cl$_2$, solvent for all other reactions was CH$_3$CN; reaction times were 2 h for all iodosylbenzene reactions and 5 min for pentafluoroiodosylbenzene reactions; products identified and quantitated by GC and GC/MS analysis.
[b]Yields of aryl iodide based on iodosylarene added; other yields based on oxidant consumed.
[c]Yields of allylic alcohol were low and variable in all cases due to rapid subsequent oxidation.
[d]Abbreviations: OTf = triflate, TPP = tetraphenylporphyrin dianion, TDCPP = tetrakis(2,6-dichlorophenyl)porphyrin dianion.
[e]Below detectable limit (<0.1%).
[f]Approximately 3% endo-epoxide present.
[g]Yields of other products not determined.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the catalytic oxidation of an organic substrate, comprising:
   (1) combining the said organic substrate, a transition metal-substituted polyoxometalate and an oxygen donor to obtain a reaction medium;
   (2) allowing the said transition metal-substituted polyoxometalate to catalyze homogeneously the oxidation of the substrate; and
   (3) obtaining an oxidized form of the said organic substrate;

wherein the said oxidation is a carbon-hydrogen bond hydroxylation reaction or an epoxidation reaction;

wherein the said organic substrate is an organic compound containing from 1 to 100 carbon atoms and at least one carbon-hydrogen bond or wherein the said organic substrate is an organic compound containing from 2 to 100 carbon atoms and at least one olefinic functionality;

wherein the said transition metal-substituted polyoxometalate is a polyoxometalate derivative having a transition metal ligated by several oxygen atoms of the metal oxide framework of the polyoxometalate and wherein the said transition metal has at least one coordination site available for coordination with either the oxygen donor or the organic substrate or both; and wherein the said transition metal is chromium, manganese, iron, cobalt, nickel, copper, technetium, rubidium, rhodium, palladium, silver, rhenium, or iridium.

2. The process of claim 1, comprising using a transition metal-substituted polyoxometalate in which the transition metal is chromium, manganese, iron, cobalt, nickel, or copper.

3. The process of claim 1, comprising using a transition metal-substituted polyoxometalate in which the transition metal is chromium, manganese, cobalt, or copper.

4. The process of claim 1, comprising using a transition metal-substituted polyoxometalate having one of the following formulae:

$$[(M)XW_xMo_yV_zO_{39}Q_aH_bLi_c; \quad \text{(i)}$$

wherein x+y+z=12;

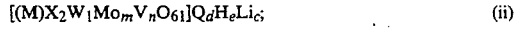

$$[(M)X_2W_1Mo_mV_nO_{61}]Q_dH_eLi_c; \quad \text{(ii)}$$

wherein l+m+ =18;

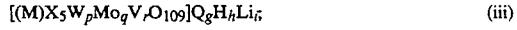

$$[(M)X_5W_pMo_qV_rO_{109}]Q_gH_hLi_i; \quad \text{(iii)}$$

where p+q+r=29;

wherein:
the values of (a+b+c) or of (d+e+f) or of (g+h+i) add up to the charge on the transition metal-substituted polyoxometalate, (M) is the said transition metal which is chromium, manganese, iron, cobalt, nickel, copper, technetium, rubidium, rhodium, palladium, silver, rhenium or iridium;

X is phosphorus, arsenic, silicon, germanium, boron, aluminum, cobalt, zinc, or iron;

Q is, independent of any other Q in any one transition metal-substituted polyoxometalate molecule, a group R$_4^2$N+, R$_4^2$P+, or R$_4^2$As+, wherein R$^2$ is independently a C$_{1-30}$ alkyl group which is straight, branched, cyclic, or a combination thereof; a C$_{6-30}$ aryl group, a C$_{6-30}$ aralkyl group, or a C$_{3-30}$ aromatic heterocyclic group.

5. The process of claim 4, wherein (M) comprises chromium, manganese, iron, cobalt, nickel or copper.

6. The process of claim 4, wherein (M) comprises chromium, manganese, cobalt, or copper.

7. The process of claim 1, wherein the said oxygen donor comprises a C$_{1-30}$ alkyl hydroperoxide, a substituted C$_{1-30}$ alkylhydroperoxide, hydrogen peroxide, a C$_{6-30}$ iodosylarene, a substituted C$_{6-30}$ iodosylarene, a $C_{1-30}$ amine-N-oxide, a substituted $C_{1-30}$ amine-N-oxide, a $C_{1-30}$ peracid, a substituted $C_{1-30}$ peracid, a hypochlorite, a halogen oxyanion, an oxaziridine, chromate, dichromate, permanganate, ruthenium or osmium tetroxide.

8. The process of claim 4, wherein Q is a tetra ($C_{1-30}$) alkyl ammonium.

9. The process of claim 4, comprising combining the organic substrate, the transition metal-substituted polyoxometalate, and the oxygen donor together with a solvent.

10. The process of claim 9, wherein the solvent comprises water, acetonitrile, hexamethylphosphoramide, dichloroethane, dichloromethane, benzene, or a mixture thereof.

11. The process of claim 4, wherein the said oxidation reaction is an epoxidation reaction.

12. The process of claim 4, wherein the said oxidation reaction is a carbon-hydrogen bond hydroxylation reaction.

13. The process of claim 4, comprising using a transition metal-substituted polyoxometalate of the formula $[(M)XW_{11}O_{39}]Q_aH_bLi_c$, wherein (M) is Co, Mn, Cu, Fe, or Cr.

14. The process of claim 4, comprising using a transition metal-substituted polyoxometalate of the formula $[(M)X_2W_{17}O_{61}]Q_dH_eLi_c$, where (M) is Co, Mn, Cu, Fe or Cr.

15. The process of claim 4, comprising using a transition metal-substituted polyoxometalate of the formula $[(M)X_5W_{29}O_{109}]Q_gH_hLi_i$, wherein (M) is Co, Mn, Cu, Fe or Cr.

16. The process of claim 4, wherein the said organic substrate comprises a straight $C_{1-100}$ alkane, a branched $C_{4-100}$ alkane, a cyclic $C_{3-100}$ alkane, a $C_{1-100}$ haloalkane, a $C_{4-100}$ branched haloalkane, a $C_{3-100}$ halocyclic alkane, a linear $C_{2-100}$ alkene, a branched $C_{4-100}$ alkene, a cyclic $C_{4-100}$ alkene, a $C_{6-100}$ arene, $C_{7-100}$ aralkane, a $C_{3-100}$ heterocyclic compound containing at least one oxygen atom or at least one sulfur atom or at least one nitrogen atom or at least one phosphorus atom, a $C_{2-100}$ ester, a $C_{2-100}$ ether, a $C_{3-100}$ ketone, $C_{1-100}$ aldehyde, $C_{2-100}$ nitrile, a $C_{1-100}$ carboxylic acid, a $C_{1-100}$ nitro compound, a $C_{1-100}$ ammonium salt, a $C_{1-100}$ thiol, a $C_{2-100}$ sulfide, a $C_{2-100}$ disulfide, a $C_{1-100}$ phosphine, a $C_{1-100}$ phosphine oxide, a $C_{3-100}$ phosphite, a $C_{3-100}$ phosphate or an arsenic or antimony analog of the said phosphine, phosphite or their oxide.

17. A polyoxometalate of one of the formulae:
$Q_w^1H_{10-w}[Co_4P_2W_{18}O_{68}]\cdot\mu H_2O$;
$Q_w^1H_{10-w}[Cu_4P_2W_{18}O_{68}]\cdot\mu H_2O$;
$Q_w^1H_{10-w}[Mn_4P_2W_{18}O_{68}]\cdot\mu H_2O$; or
$Q_w^1H_{10-w}[Fe_4P_2W_{18}O_{68}]\cdot\mu H_2O$;

wherein:
$Q^1$ is a quaternary salt, $R_4^3N^+$, $R_4^3P^+$, or $R_4^3As^+$,
$R^3$ is independently a $C_{1-30}$ alkyl, $C_{6-30}$ aryl, or $C_{7-30}$ aralkyl, and wherein at least one $R^3$ is a $C_{8-30}$ alkyl when all $R^3$ in a molecule $Q^1$ are $C_{1-30}$ alkyl and $Q^1$ is $R^3N^+$;
w is an integer of from 0 to 10; and
$\mu$ is an integer of from 0 to 50; or
wherein at least one group $Q^{(1)+}$ or $H^+$ is exchanged for a $Li^+$ ion.

18. A polyoxometalate of one of the formulae:

$Q_w^2H_{16-w}[Co_4P_4W_{30}O_{112}]\cdot\mu H_2O$;

$Q_w^2H_{16-w}[Cu_4P_4W_{30}O_{112}]\cdot\mu H_2O$;

$Q_w^2H_{16-w}[Mn_4P_4W_{30}O_{112}]\cdot\mu H_2O$; or $Q_w^2H_{16-w}[Fe_4P_4W_{30}O_{112}]\cdot\mu H_2O$;

wherein:
$Q^2$ is a quaternary salt, or $R_4^4N^{30}$, $R_4^4P^+$, or $R_4^4As^+$, and wherein $R^4$ is independently a $C_{1-30}$ alkyl, $C_{6-30}$ aryl, or a $C_{7-30}$ aralkyl, and wherein at least one $R^4$ is a $C_{8-30}$ alkyl when all groups $R^4$ are $C_{1-30}$ alkyl in a molecule $Q^2$ and $Q^2$ is $R_4^4N^+$;
w is an integer from 0 to 10; and
$\mu$ is an integer from 0 to 50; or wherein at least one group $Q^{(2)+}$ or $H+$ is exchanged for a $Li^+$ ion.

19. A polyoxometalate of one of the formula:

$Q_w^3H_{8-w}[S_2Nb_6W_{18}O_{77}]\cdot\mu H_2O$ wherein:
$Q^3$ is a quaternary salt, $R_4^5N^+$, $R_4^5P^+$, or $R_4^5As^+$, and wherein $R^5$ is a $C_{1-30}$ alkyl group, a $C_{6-30}$ aryl, or a $C_{7-30}$ aralkane group, and wherein at least one $R^5$ is a $C_{8-30}$ alkyl when all groups $R^5$ in a molecule $Q^3$ are $C_{1-30}$ alkyl and $Q^3$ is $R_4^5N^+$;
w is an integer of from 0 to 8; and
$\mu$ is an integer of from 0 to 50; or
wherein at least one group $Q^{(3)+}$ or $H^+$ is exchanged for a $Li^+$ ion.

20. A polyoxometalate of the formula:
$Q_w^4H_{12-w}[(M)_3P_2W_{18}O_{68}]\cdot\mu H_2O$ wherein:
(M) is $Co^{II}$, $Mn^{II}$, $Cu^{II}$, or $Fe^{II}$; and
$Q^4$ is a quaternary salt or $R_4^6N^+$, $R_4^6P^+$, or $R_4^6As^+$, where $R^6$ is a $C_{1-30}$ alkyl group, a $C_{6-30}$ aryl group, or a $C_{7-30}$ aralkyl group.

* * * * *

UNITED STATES PATENT AND TRADEMARK OFFICE
CERTIFICATE OF CORRECTION

PATENT NO.   :  4,864,041
DATED        :  September 5, 1989
INVENTOR(S)  :  Hill It is certified that error appears in the above-identified patent and that said Letters Patent is hereby corrected as shown below:

Column 2, line 16, "(e.g., alkanes))" should read

--(e.g., alkanes)--.

Column 6, line 12, "contain" should read --containing some of the--.

Column 7, line 38, insert --p+q+r=29.--;

line 40, "(gh+i)" should read --(g+h+i)--.

Column 8, line 5, "$Q_2^1$" should read --$Q_{w1}$--;

line 9, "$R^3As^+$" should read --$R_4^3As^+$--;

line 21, "in this document, is the" should read

--in this document, $\mu$ is the-- line 56, "$R^5N+$" should read --$R_4^5N^+.$--.

line 63, "$Q_w^3H_{8-w}Si_2NbW_{18}O_{77}]\cdot H_2O$" should read

--$Q_w^3H_{8-w}[Si_2Nb_6W_{18}O_{77}]\cdot \mu H_2O$--.

UNITED STATES PATENT AND TRADEMARK OFFICE
CERTIFICATE OF CORRECTION

PATENT NO. : 4,864,041

DATED : September 5, 1989

INVENTOR(S) : Hill

It is certified that error appears in the above-identified patent and that said Letters Patent is hereby corrected as shown below:

Column 9, line 4, "Qhd" should read --$Q^{(4)+}$--;

line 5, delete "w(4)+";

line 9, insert --$\mu$-- before "$H_2O$;"

line 35, "reacts with MnII to form (MnII)" should read --reacts with $Mn^{II}$ to form ($Mn^{II}$)--.

Column 11, line 15, "the heteroatom has been hydrogen bond" should read --the heteroatom has been oxidized together with the results of the carbon hydrogen bond--.

Column 12, line 57, delete "published in "Organic Synthesis" ".

UNITED STATES PATENT AND TRADEMARK OFFICE
CERTIFICATE OF CORRECTION

PATENT NO. : 4,864,041

DATED : September 5, 1989

INVENTOR(S) : Hill

It is certified that error appears in the above-identified patent and that said Letters Patent is hereby corrected as shown below:

Column 13, line 7, "$(MnPW_{11}O_{39})(H)NBu_4)_4$" should read --$(MnPW_{11}O_{39})(H)(NBu_4)_4$--;

line 20, ")NB" should read --)(NB--;

line 33, "(H)NB" should read --(H)(NB--;

line 45, "(H)NB" should read --(H)(NB--;

line 62, in Table 1, "$(CoPW_{11})_{39})$" should read --$(CoPW_{11}O_{39})$--;

line 68, "(H)NB" should read --(H)(NB--.

UNITED STATES PATENT AND TRADEMARK OFFICE
CERTIFICATE OF CORRECTION

PATENT NO. : 4,864,041

DATED : September 5, 1989

INVENTOR(S) : Hill

It is certified that error appears in the above-identified patent and that said Letters Patent is hereby corrected as shown below:

Column 14, line 12, "(H)NB" should read --(H)(NB--;

line 24, "(H)NB" should read --(H)(NB--;

line 36, "(H)NB" should read --(H)(NB--;

line 48, "(H)NB" should read --(H)(NB--;

line 53, "a" should read --an--.

Column 15, line 5, "(H)NB" should read --(H)(NB--;

line 18, "(H)NB" should read --(H)(NB--;

line 31, "(H)NB" should read --(H)(NB--;

line 36, "7%" should read --17%--;

line 44, "(H)NB" should read --(H)(NB--;

line 57, "(H)NB" should read --(H)(NB--;

UNITED STATES PATENT AND TRADEMARK OFFICE
CERTIFICATE OF CORRECTION

PATENT NO. : 4,864,041

DATED : September 5, 1989

INVENTOR(S) : Hill

It is certified that error appears in the above-identified patent and that said Letters Patent is hereby corrected as shown below:

Column 16, line 12, "(H)NB" should read --(H)(NB--;

line 25, "(H)NB" should read --(H)(NB--;

line 38, "(H)NB" should read --(H)(NB--;

line 50, "(H)NB" should read --(H)(NB--;

line 60, in Table II, second line, "$(MnPW_{11})_{39})^{5-}$" should read --$(MnPW_{11}O_{39})^{5-}$--.

Column 17, line 33, "$O_{30}$" should read --$O_{39}$--.

Column 18, line 54, insert --<-- after "(least stable)".

Column 19, line 34, "C. Cyclooctene" should read

--D. Cyclooctene--.

Column 20, line 33, "$O_{39}$" should read --$O_{39}$]--;

line 39, "l+m+=18" should read --l+m+n=18--.

Column 21, line 24, "Qa" should read --$Q_a$--;

line 28, "Qd" should read --$Q_d$--;

line 32, "Qg" should read --$Q_g$--.

UNITED STATES PATENT AND TRADEMARK OFFICE
CERTIFICATE OF CORRECTION

PATENT NO. : 4,864,041

DATED : September 5, 1989

INVENTOR(S) : Hill

Page 6 of 6

It is certified that error appears in the above-identified patent and that said Letters Patent is hereby corrected as shown below:

Column 22, line 4, "$As^+,$" should read --$As^+,$ and--;

line 8, "$R^3$" should read --$R_4^3$--;

line 23, delete "or" after "salt" and "$N^{30}$" should read --$N^+$--.

line 29, "$Q(^{(2)+}$" should read --$Q^{(2)+}$--;

line 34, in the formula, "$S_2$" should read --$Si_2$--;

line 34, insert --;-- at end of the formula;

line 36, "$R_4^5P^+$" should read --$R_4^5P^+$--;

line 43, "Q(3)" should read --$Q^{(3)}$--.

Signed and Sealed this

Twenty-ninth Day of October, 1991

Attest:

HARRY F. MANBECK, JR.

*Attesting Officer*

*Commissioner of Patents and Trademarks*